(12) United States Patent
Brown et al.

(10) Patent No.: US 6,765,109 B1
(45) Date of Patent: Jul. 20, 2004

(54) PREPARATION OF S-ARYL-CYSTEINE AND ITS DERIVATIVES

(75) Inventors: Jack D. Brown, Westminster, CO (US); Hiralal N. Khatri, Louisville, CO (US); Peter J. Harrington, Louisville, CO (US); Dave A. Johnston, Louisville, CO (US); Robert J. Topping, Longmont, CO (US); Richard R. Dauer, Longmont, CO (US); Gary K. Rowe, Littleton, CO (US)

(73) Assignee: Roche Colorado Corporation, Boulder, CO (US)

( * ) Notice: Subject to any disclaimer, the term of this patent is extended or adjusted under 35 U.S.C. 154(b) by 307 days.

(21) Appl. No.: 09/713,134

(22) Filed: Nov. 14, 2000

Related U.S. Application Data

(62) Division of application No. 09/339,721, filed on Jun. 24, 1999, now Pat. No. 6,229,041.
(60) Provisional application No. 60/091,102, filed on Jun. 29, 1998, and provisional application No. 60/096,142, filed on Aug. 11, 1998.

(51) Int. Cl.$^7$ ...................... C07C 229/36; C07C 227/32
(52) U.S. Cl. ........................ 560/9; 560/155; 560/157; 562/426
(58) Field of Search ........................... 560/9, 155, 157; 562/426

(56) References Cited

U.S. PATENT DOCUMENTS

| | | | |
|---|---|---|---|
| 5,554,653 A | * | 9/1996 | Hui et al. .................... 514/605 |
| 6,130,348 A | * | 10/2000 | Hilpert ......................... 560/17 |

FOREIGN PATENT DOCUMENTS

| | | |
|---|---|---|
| EP | 0 897 911 A1 | 2/1999 |
| WO | WO 98/45271 | 10/1998 |

OTHER PUBLICATIONS

Chenault, H. K. et al "Kinetic resolution of unnatural and rarely occurring amino acids" J. Am. Chem. Soc. vol 111, no 16, pp. 6354–6364, 1989.*

Liu, J., et al "Total synthesis of (–)–eudistomin F" Heterocycles, vol 31, no 2, pp. 229–232, 1990.*

Sasaki et al., "A Novel Approach to the Synthesis of Optically Pure Now Protein α–Amino Acids in Both L and D Configurations from L–Serine," *Tetrahedron Letters*, 1987, v. 28, pp. 6069–6072.

Marzoni et al., "A Convenient, Large Scale Synthesis of N–CBZ–(S–Phenyl)–L–Cysteine," *Synthetic Communications*, 1995, v. 25(16), pp. 2475–2482.

Hichman et al., "Synthesis of Aromatic S–Substituted Derivatives of N–Acetyl–L–Cysteine," *Aust. J. Chem.*, 1985, v. 38, pp. 899–904.

Knight and Sibley, "Total Synthesis of (–)–Slaframine from (2R,3S)–3–Hydroxyproline," *J. Chem. Soc., Perkin Trans. I*, 1997, pp. 2179–2187.

Nakamura et al., A General and Efficient Synthesis of Optically Pure S–Arylmercapturates, *Heterocycles*, 1995, v. 41, pp. 1131–1134.

Ciattini, et al., "A New , Palladium–Catalyzed Synthesis of Aromatic Mercapturic Acid Derivates," *Tetrahedron Letters*, 1995, v. 36, pp. 4133–4136.

(List continued on next page.)

*Primary Examiner*—James O. Wilson
*Assistant Examiner*—Leigh C. Maier
(74) *Attorney, Agent, or Firm*—Faegre & Benson LLP

(57) ABSTRACT

The present invention provides a method for preparing S-aryl cysteine. Specifically, the present invention provides enantioselective method for preparing S-aryl cysteine starting from cystine, cysteine or serine amino acid. The methods of the present invention provides S-aryl cysteine in enantiomeric excess of greater than about 96%.

13 Claims, 3 Drawing Sheets

$P^1$ = H or N-protecting group
$P^2$ = H or Carboxylic Acid protecting group
Ar = aryl group
X = leaving group
PTC = phase transfer catalyst

OTHER PUBLICATIONS

Hanzlik et al., "Synthesis of Mercapturic Acid Derivatives of Putative Toxic Metabolites of Bromobenzene," *J. Org. Chem.*, 1990, v. 55, pp. 2736–2742.

Knight and Sibley, "A Total Synthesis of (−)-Slaframine from (+)-CIS-(2R,3S)-3-Hydroxyproline," *Tetrahedron Letters*, 1993, v. 34, pp. 6607–6610.

Kita et al., "Chemistry of O-Silylated Keteine Acetals: Biomimetic Synthesis of CIS-B-Lactams," *Tetrahedron Letters*, 1989, v. 30, pp. 729–730.

Zbarsky and Young, "Mercapturic Acids I. The Synthesis of Phenyl–L–Cysteine and L–Phenylmercapturic Acid," *J. Bio. Chem.*, 1943, v. 151, pp. 211–215.

du Vigneaud et al., "Acetylation in Vivo of p–Bromophenyl–d–Cysteine," *J. Biol. Chem.*, 1941, v. 138, pp. 369–374.

Zervas et al., "Preparation and Disulfide Interchange Reactions of Unsymmetrica Open–Chain Derivatives of Cystine," *J. Am. Chem. Soc.*, 1959, v. 81, pp. 1729–1734.

du Vigneaud et al., "The Reduction of Cystine in Liquid Ammonia by Metallic Sodium," *J. Amer. Chem. Soc.*, 1930, v. 52, pp. 4500–4504.

Wieland and Sarges, "ZUR Synthese von Tryptathioninpeptiden," *Justus Liebigs Am. Chem.*, 1962, v. 658, pp. 181–193.

Hata and Watanabe, "Reaction of Aziridinecarboxylic Acids with Thiols in Aqueous Solution. The Formation of β–Amino Acid," *Tetrahedron*, 1987, v. 43, pp. 3881–3888.

Belokon et al., "Asymetric Synthesis of β–Substituted α–Amino Acids via a Chiral nl$^{11}$ Complex of Dehyroalanine," *Tetrahedron*, 1988, v. 44, pp. 5507–5514.

Campbell, "Reduction of disulfides with Copper. Preparation of Some Thioethers," *J. Org. Chem.*, 1962, v. 27, pp. 2207–2209.

Clarke and Inouye, "the Alkaline Deamination of Derivatives of Cysteine," *J. Biol. Chem.*, 1931, v. 94, p. 541–550.

Adams and Ferretti, "Thioethers from Halogen Compounds and Cuprous Mercaptides, IIth," *J. Am. Chem. Soc.*, 1959 v. 81, pp. 4927–4931.

Campbell, "Synthesis of Thioethers, Amide Solvent–Promoted Nucleophilic Displacement of Halide by Thiolate Ion," *J. Org. Chem.*, 1964, v. 29, pp. 1830–1833.

Esaki et al., "Enzymatic Synthesis of S–Substituted 1–Cysteines with Tryptophan Synthase of *Escherichia coli*, " Agric, Biol. Chem., 1983, v. 47(12), pp. 2861–2864.

Chowdhry et al., "Cobalt Assisted Cleavage of S–S Bonds and a Base Free Synthesis of Mercaptureic Acids" Tet. Lett. vol. 38, No. 12, pp. 2149–2151 (1997).

Raymond J. S. Hickman et al., *Australian Journal of Chemistry*, 1985, 38, 899–904.

Stephen W. Kaldor et al., *J. Med. Chem*, 1997, 40, 3979–3985.

Portevine, B. et al., "Dual Inhibition of Human Leukocyte Elastase and Lipid Peroxidation: In Vitro and In Vivo Activities of Azabicycloä22.2.2üoctane and Perhydroindole Derivatives," Journal of Medicinal Chemistry, American Chemical Society, Washington, U.S., vol. 40, (1997), pp. 1906–198, XP002935499.

* cited by examiner

PREPARATION OF S-ARYL-CYSTEINE AND ITS DERIVATIVES

CROSS-REFERENCE TO RELATED APPLICATIONS

This application is a divisional of U.S. patent application Ser. No. 09/339,721, filed Jun. 24, 1999, now U.S. Pat. No. 6,229,041, which claims the benefit of U.S. Provisional Application Nos. 60/091,102, filed Jun. 29, 1998, and No. 60/096,142, filed Aug. 11, 1998.

FIELD OF THE INVENTION

The present invention relates to a process for preparing an enantiomerically enriched S-aryl cysteine and its derivatives. Specifically, the process of the present invention provides S-aryl cysteine and its derivatives in enantiomeric excess of greater than about 96%.

BACKGROUND OF THE INVENTION

S-aryl cysteines are useful compounds in the biological study of metabolism, and they are useful intermediates in a synthesis of a variety of pharmaceutically active compounds. For example, S-aryl cysteine derivatives (mercapturic acids) are useful for studying the xenobiotics metabolic pathways. L. F. Chasseaud, *Drug Metab. Rev.*, 1973, 2, 185. In addition, chiral S-aryl-L-cysteines have been used successfully to target the human immunodeficient virus (HIV) as a therapy for the treatment of AIDS. Kaldor et al., *J. Med. Chem.* 1997, 40 (24), 3979–3985.

Many currently available synthetic methods for S-aryl cysteine involve preparation of racemic mixtures. There are, however, a number of disadvantages associated with racemic mixtures of such compound. A racemic mixture of S-aryl cysteine results in production of racemic drugs. It is well known that certain physiological properties of chiral drugs are dependent upon stereochemistry of the drug and the undesired side-effects to are often attributed to the presence of the undesired stereoisomer of the chiral drug. Accordingly, a high enantioselective synthesis of a chiral drug will result in a drug having a desired therapeutic activity with a reduced amount of undesired side-effects. Of course, the synthesis of a chiral drug can include a step of separating a racemic mixture; however, this is often time consuming and costly. In addition, racemic synthesis requires discarding one half of the compound unless the undesired isomer can be converted to a desired isomer. Moreover, not all racemic compounds can be resolved to provide a satisfactory yield of a desired enantiomer.

Current methods for enantioselective synthesis of S-aryl cysteine involve enzymatic methods (See, for example, Japanese Patent No. 58,146,287 and European Patent Application No. EP 754,759, which are assigned to Mitsui Toatsu Chemicals, Inc.) and are applicable to preparation of only a limited number of S-aryl cysteines.

Most of the current chemical synthetic methods for enantioselective preparation of S-aryl cysteine result in a racemic mixture, use elaborate reagents dramatically increasing the overall cost, or result in unacceptable levels of enantioselectivity to be useful in a pharmaceutical process.

Recently, Knight and Sibley (D. W. Knight and A. W. Sibley, *J. Chem. Soc., Perkin Trans.* 1, 1997, 2179–2187) reported that the displacement of N-benzyloxycarbonyl-O-p-toluenesulfonyl serine methyl ester (or methyl (S)-2-p-benzyloxycarbonylamino-3-methylsulfonyloxypropanoate) with freshly prepared sodium thiophenylate in DMF at about 0° C. afforded the desired N-benzyloxycarbonyl-S-phenyl-L-cysteine methyl ester (or methyl (R)-2-benzyloxycarbonylamino-3-phenylthiopropanoate) in 98% yield providing a reported optical rotation of $[\alpha]^{20}_D$ −17.2 (c, 1.8; MeOH). No enantiomeric ratio of the product was reported. Furthermore, the use of sodium phenolate, prepared from sodium hydride, thiophenol and DMF is not amenable to large scale manufacture.

Therefore, there is a need for an efficient, concise and enantioselective method suitable for the large scale manufacture of S-aryl cysteine using relatively inexpensive reagents.

SUMMARY OF THE INVENTION

The present invention is directed to a method for preparing S-aryl cysteines of the formula:

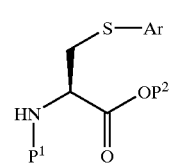

I where Ar is an aryl, $P^1$ is H or an amine protecting group and $P^2$ is H or a carboxylic acid protecting group.

Preferably Ar is $C_5$–$C_{20}$ aryl.

Preferably $P^1$ is an amine protecting group, and more preferably $P^1$ is benzyloxycarbonyl (i.e., —C(=O)OCH$_2$C$_6$H$_5$) or methoxycarbonyl (i.e., —C(C=O)OCH$_3$).

Preferably $P^2$ is a carboxylic acid protecting group, and more preferably $P^2$ is methyl.

In one embodiment of the present invention, a thiolate of the formula:

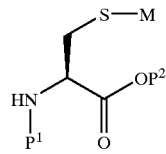

II is reacted with an aryl halide of the formula Ar—X$^1$, where M is a metal, X$^1$ is a halide and Ar is an aryl as defined above.

The thiolates of compound II can be generated by contacting cystine or cysteine with a coupling reagent. A coupling reagent is selected from the group consisting of a metal, metal oxide, metal salt and mixtures thereof. Preferably the coupling agent is selected from the group consisting of copper, copper halide, copper oxide, zinc, zinc halide, zinc oxide, aluminum, aluminum halide, aluminum oxide, iron, iron oxide, iron halide, cobalt, cobalt oxide, cobalt halide, tin, tin oxide, tin halide, potassium, potassium oxide, potassium halide, sodium, sodium oxide, sodium halide and mixtures thereof. More preferably, the coupling agent is selected from the group consisting of copper, copper halide, copper oxide and mixtures thereof. And most preferably, the coupling agent is selected from the group consisting of copper, cupric bromide, cupric oxide, cupric chloride, cupric iodide, cuprous bromide, cuprous chloride, cuprous iodide and mixtures thereof. Typically, the thiolate is generated in situ and is used without further purification.

A variety of aryl halides can be reacted with the thiolate to produce S-aryl cysteine compounds. Preferably, aryl halide is phenyl bromide.

The reaction may be conducted in the presence of a reaction solvent. Preferably, the reaction solvent is selected from the group consisting of dimethylacetamide, dimethyl formamide (DMF), dimethyl sulfoxide (DMSO), diethylacetamide, dimethylbutyramide, and N-methyl-2-pyrrolidone.

In another embodiment of the present invention, a compound of the formula:

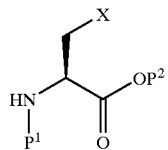

III where X is a halide, mesylate or tosylate, is contacted with an aryl thiol (i.e., Ar—SH) in the presence of a base. Preferably the base is selected from the group consisting of sodium hydroxide, sodium bicarbonate, and potassium carbonate. X is a leaving group which is displaced by the sulfur group of the aryl thiol. Preferably, X is mesylate or tosylate. In a particular aspect of the present invention, the compound is prepared from serine. For example, protection of the amine group and the carboxylic acid group followed by conversion of the hydroxy group to a leaving group produces the desired compound, which can undergo a substitution reaction with an aryl thiol to produce the desired S-aryl cysteine.

The method may further involve the addition of a phase transfer catalyst. Preferably, the phase transfer catalyst is selected from the group consisting of Aliquat® 336 (i.e., tricaprylylmethylammonium chloride, a mixture of $C_8$ and $C_{10}$ chains with $C_8$ predominating), TBAB, and TBPB.

Preferably, the method of the present invention produces S-aryl cysteine enantioselectively. More preferably, the method produces S-aryl cysteine in enantiomeric excess of greater than about 96%, still more preferably greater than about 98%, and most preferably greater than about 99.5%.

DETAILED DESCRIPTION OF THE INVENTION

Definitions

Figure 1:
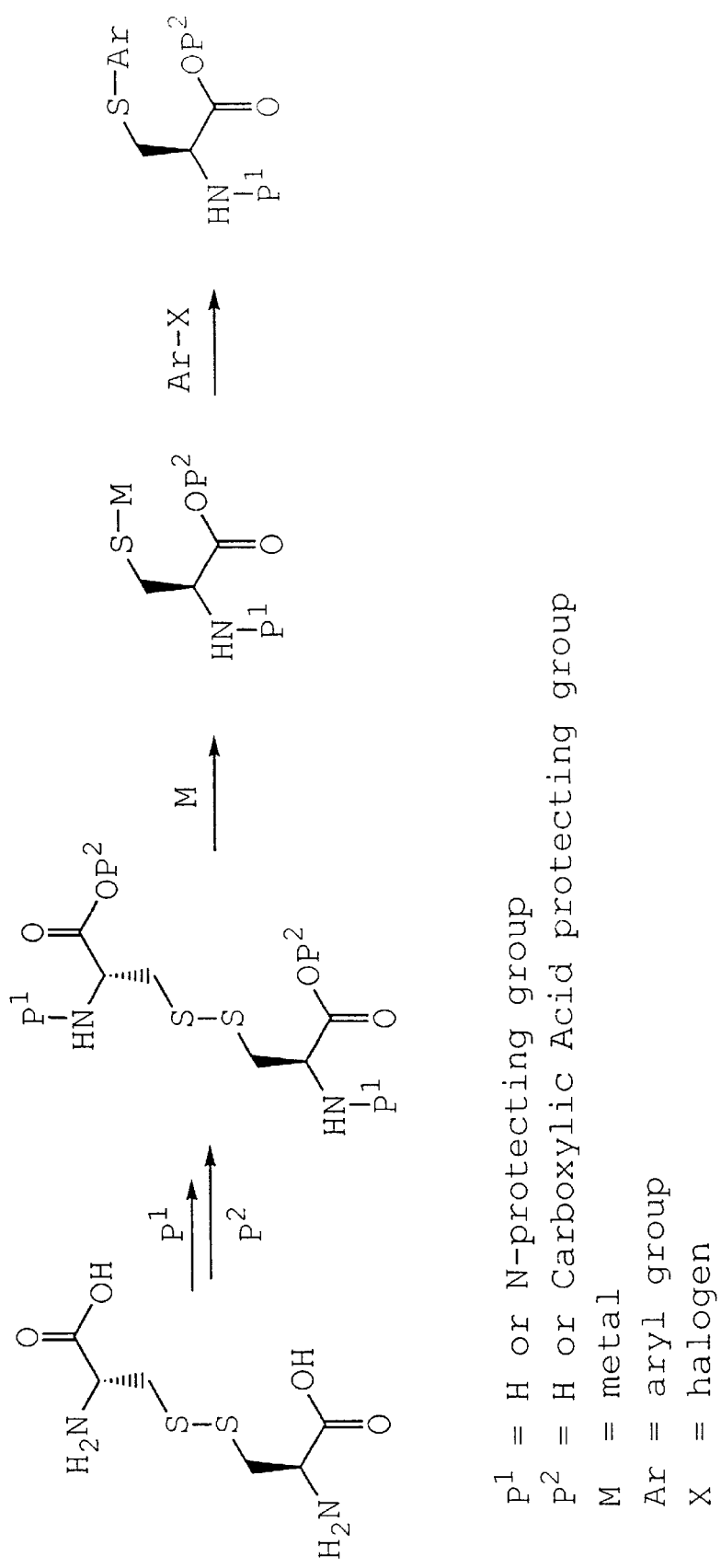
FIG. 1 illustrates one embodiment of the present invention for preparing a S-aryl cysteine compound from cystine.

"Aryl" means an aromatic group which has at least one ring which has a conjugated pi electron system and includes, without limitation, carbocyclic aryl, aralkyl, heterocyclic aryl, biaryl groups and heterocyclic biaryl, all of which can be optionally substituted.

"Heterocyclic aryl groups" refer to groups having at least one heterocyclic aromatic ring containing from 1 to 3 heteroatoms in the ring with the remainder being carbon atoms. Suitable heteroatoms include, without limitation, oxygen, sulfur, and nitrogen. Exemplary heterocyclic aryl groups include furanyl, thienyl, pyridyl, pyrrolyl, N-alkyl pyrrolyl, pyrimidyl, pyrazinyl, imidazolyl, benzofuranyl, quinolinyl, and indolyl.

The term "S-aryl" refers to a substituent wherein an aromatic group is bonded to a sulfur atom. "S-aryl" group may also be referred to as an "aryl thioether" group. The term "S-arylation" refers to the process of forming the S-aryl group.

The term "arylthiol" refers to an aryl group as defined above, which is attached to any group of organic compound resembling an alcohol, but with the oxygen of the hydroxyl group being replaced by sulfur.

A "metal" refers to an element that forms positive ions when its compounds are in solution and whose oxides form hydroxides rather than acids with water. Metals may fall into the following classifications which are not mutually exclusive: alkali metals, alkaline-earth metals, transition metals, noble metals, platinum metals, rare metals, rare-earth metals, actinide metals, light metals, and heavy metals. Some of these metals include aluminum, iron, copper, cobalt, potassium, sodium, tin and zinc. See "Hawley's Condensed Chemical Dictionary", 11th ed., revised by N. Irving Sax and Richard J. Lewis, Sr., Van Nostrand Reinhold Company, New York, p. 748 (1987).

The term "catalyst" refers to any substance of which a fractional percentage notably affects the rate of a chemical reaction without itself being consumed or undergoing a chemical change, as defined in "Hawley's Condensed Chemical Dictionary", vide supra.

The term "stoichiometric" refers to the use or addition of an equivalent mole ratio or amount of a reagent relative to a selected substrate, molecule, or compound in a reaction.

The term "chiral" refers to a compound or molecule having a nonsuperimposable mirror image or being asymmetric.

The term "enantiomeric excess" refers to a difference between the amount of one enantiomer and the amount of the other enantiomer that is present in the product mixture. Thus for example, enantiomeric excess of 96% refers to a product mixture having 98% of one enantiomer and 2% of the other enantiomer.

The following abbreviations and terms are used herein:
"CBZ" means benzyloxycarbonyl (i.e., carbobenzyloxy).
"DMF" means dimethylformamide.
"DMSO" means dimethyl sulfoxide.
"Tosylate" or "Tos" means p-toluenesulfonate ester.
"Mesylate" or "Ms" means methanesulfonate ester.
"TBPB" means tetrabutylphosphonium bromide.
"TBAB" means tetrabutylammonium bromide.
"PTC" means phase transfer catalysis or catalyst.
"A/N" and "AN" means area normalized.
"HPLC" means high performance liquid chromatography.
"LC" means liquid chromatography.

The present invention provides novel processes for stereoselective synthesis of S-aryl cysteine and its derivatives, including S-aryl-L-cysteine and its derivatives. S-aryl cysteines are useful intermediates in a variety of pharmaceutically active compounds.

Cysteine is an amino acid having a chiral center alpha to the carboxylic acid moiety. The compounds produced by the processes of the present invention can be used as intermediates in the synthesis of drugs to treat a variety of illnesses, including the treatment of viral infections.

It is well known that certain physiological properties of chiral drugs are dependent upon stereochemistry of the drug and the undesired side-effects are often attributed to the presence of an undesired stereoisomer of the chiral drug.

Accordingly, a high enantioselective synthesis of a chiral compound or an intermediate which is used as a drug will result in high therapeutic activity while reducing undesired side-effects. Current synthetic methods for S-phenyl cysteine and its derivatives, however, provide unacceptable levels of stereochemical control.

The present invention is, thus, directed to stereoselective synthetic techniques for S-phenyl cysteine and its derivatives. Specifically, the process of the present invention provides enantiomerically enriched S-aryl L- or D-cysteine. Preferably, the process of the present invention provides S-aryl cysteine in enantiomeric excess of greater than about 96%, more preferably greater than about 98%, and most preferably greater than about 99.5%. Unless the context requires otherwise, reference to any compound is to be considered as a reference to an individual enantiomer of the compound, and to racemic or non-racemic mixtures thereof.

As shown in FIG. 1, one embodiment of the present invention provides a method for producing S-aryl cysteine by contacting cystine with a coupling agent and contacting the resulting compound with an aryl halide for a time and under conditions effective to produce S-aryl cysteine. A "coupling agent" is any compound or moiety in which the presence of such compound or moiety in the reaction mixture produces the S-aryl cysteine from an aryl halide and an appropriate cysteine moiety equivalent. When cystine is used as a starting material in a coupling reaction, the amount of aryl halide used is preferably from about 1 equiv. to about 7 equiv., more preferably from about 2 equiv. to about 6 equiv., still more preferably from about 2 equiv. to about 4 equiv., and most preferably about 3 equiv. Preferably the halide in aryl halide is selected from the group consisting of iodide, bromide and chloride, more preferably from the group consisting of bromide and iodide, and most preferably the halide is bromide. Without being bound by any theory, it is believed that contacting cystine with a coupling agent results in cleavage of the disulfide bond (i.e., a sulfur-sulfur bond), generating a metal thiolate of cystine which undergoes a coupling reaction to form the desired product and a metal halide. Thus, it is believed that any coupling agent which can cleave the disulfide bond can be used in the process of the present invention. The temperature of the reaction is preferably from about 80° C. to about 150° C., more preferably from about 100° C. to about 130° C., and most preferably from about 115° C. to about 125° C. The reaction time can vary depending upon the identity of the metal and/or the aryl halide; but generally it has been found that the reaction time of at least about 1 h produces the desired product in a relatively high yield, preferably at least about 15 h, and more preferably at least about 18 h.

Figure 2:
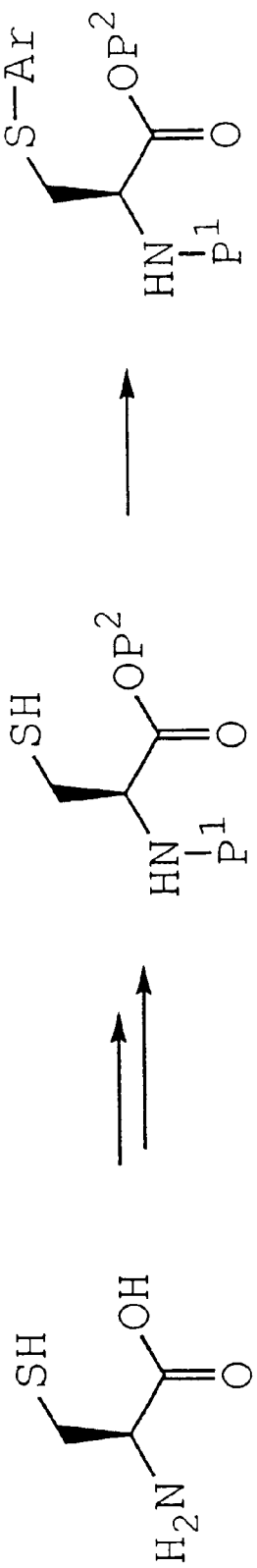
FIG. 2 illustrates another embodiment of the present invention for preparing a S-aryl cysteine compound which utilizes cysteine.

As shown in FIG. 2, another embodiment of the present invention provides a method for producing S-aryl cysteine by contacting cysteine with an aryl halide in the presence of a coupling agent. When cysteine is used as a starting material in a coupling reaction, the amount of aryl halide used is preferably from about 1 equiv. to about 5 equiv., more preferably from about 1.1 equiv. to about 4 equiv., still more preferably from about 1.2 equiv. to about 3 equiv., and most preferably about 1.5 equiv. It has been found that the production of S-aryl cysteine by this method is facilitated by heating the mixture. Preferably, the reaction temperature is from about 80° C. to about 150° C., more preferably from about 100° C. to about 130° C., and most preferably from about 115° C. to about 125° C.

A method of the present invention for producing S-aryl cysteine can include the presence of a coupling agent. Without being bound by any theory, it is believed that the coupling agent generates the reactive thiolate compound of the formula:

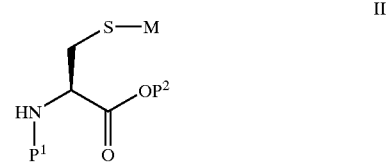

II from cystine or cysteine, where M is a metal, $P^1$ is H or an amine protecting group and $P^2$ is H or a carboxylic acid protecting group. It will be appreciated that the above structure merely represents an idealized representation of thiolate. The exact structure of the thiolate can be a dimer, trimer or other polymeric form of the reactive intermediate or a metal containing more than one thiolate group. Moreover, the metal can also contain other ligands such as solvent molecules or other species which may be present in the reaction mixture. Any metal or its derivative which produces a coupled product from the thiolate and an aryl halide can be used in the present invention. Generally, a coupling agent is selected from the group consisting of a metal, metal oxide, metal salt and mixtures thereof. As used in this invention, a "metal salt" refers to any organic or inorganic metal species in which the oxidation state of the metal is not zero. Exemplary metal salts include, ferrocene, ferric chloride, ferric acetate, ferrous acetate, ferrous acetylacetonate, ferric acetylacetonate, ferrous chloride, cupric iodide, cuprous iodide, cupric bromide, cuprous bromide, cupric chloride, cuprous chloride, cupric fluoride, cupric acetate, cupric acetylacetonate, cupric hydroxide, copper sulfate, cupric cyanide, cupric oxide, and cuprous oxide. Preferably the coupling agent is selected from the group consisting of copper, copper salts including copper halides and copper oxides, zinc, zinc halide, zinc oxide, aluminum, aluminum halide, aluminum oxide, iron, iron oxide, iron halide, cobalt, cobalt oxide, cobalt halide, tin, tin oxide, tin halide, potassium, potassium oxide, potassium halide, sodium, sodium oxide, sodium halide and mixtures thereof. More preferably, the coupling agent is selected from the group consisting of copper; copper salts, such as copper halides and copper oxides; and mixtures thereof. And most preferably, the coupling agent is selected from the group consisting of copper, cupric bromide, cupric oxide, cupric chloride, cupric iodide, cuprous bromide, cuprous chloride, cuprous iodide, cuprous cyanide, cuprous oxide, cupric fluoride, cupric acetate, cupric acetylacetonate, cupric sulfate, cupric hydroxide and mixtures thereof.

A method of the present invention for producing S-aryl cysteine can further include an oxidizing agent. An oxidizing agent is any compound which can generate the reactive species of the coupling agent. Preferably oxidizing agent is selected from the group consisting of bromine, iodine, chlorine and mixtures thereof.

Without being bound by any theory, it is believed that while the method of the present invention can proceed with copper (0) metal similar to those of the standard Ullman reactions, the method of the present invention can also include the presence of a metal salt ($M_aX_b$), where a and b represent corresponding amount of M or X depending on the oxidation state of M and X. The metal salt can be an inorganic salt such as metal halides including copper (I) or (II) bromide, chloride, iodide, and halides of other above described metals, or an organic salt such as copper (I) or (II) acetylacetonate, acetate and organic salt of other above described metals. Without being bound by any theory, it is believed that when copper (0) and copper (II) salt are present together, copper (0) and copper (II) species undergo disproportionation to form copper (I) species, which may be the active species for the process. Surprisingly and unexpectedly, it has been found that while Copper (0) or other metal can be an effective coupling agent, the presence of Copper (I) or Copper (II) salt, such as copper (I) or (II) bromide, in addition to Copper (0) increases the rate of reaction. Preferably, from about 0 mol % to about 100 mol % of copper (I) or (II) bromide, relative to aryl halide, is added, more preferably from about 0.2 mol % to about 7 mol %, and most preferably about 1 mol % to about 6 mol %. Typically about 6 mol % of copper (I) or copper (II) bromide is added. It should be recognized that other functional groups present in cystine or cysteine can be protected or unprotected.

Typically, the amount of coupling agent, relative to aryl halide, used is from about 0.3 equiv. to about 1 equiv., preferably from about 0.5 equiv. to about 0.75 equiv., and more preferably from about 0.6 equiv. to about 0.7 equiv. It has been found that after the reaction, the coupling agent or the resulting product of the coupling agent, e.g., copper (I) salt such as copper bromide, may be isolated and recycled to be used in another coupling reaction. In this manner, the cost of coupling agent and the disposal cost of the resulting coupling agent product, e.g., copper (I) bromide, can be substantially reduced.

Although the method of the present invention can be conducted in the absence of a solvent, it has been found that the presence of a relatively high boiling point solvent provides a reaction medium which can be heated to a desired temperature. Thus, the solvent has boiling point higher than the desired reaction temperature. Preferably the solvent is selected from the group consisting of acetonitrile, glymes, dimethylacetamide, dimethylformamide, diethylacetamide, dimethylbutyramide, dimethyl sulfoxide and N-methyl-2-pyrrolidone, and more preferably the solvent is selected from the group consisting of dimethylformamide and dimethyl sulfoxide. The reaction time can vary depending upon the identity of the metal oxide and/or the aryl halide, but generally it has been found that the reaction time of at least about 1 h produces a relatively high yield of the desired product with high enantioselectivity, preferably at least about 15 h, and more preferably at least about 18 h.

Figure 3:
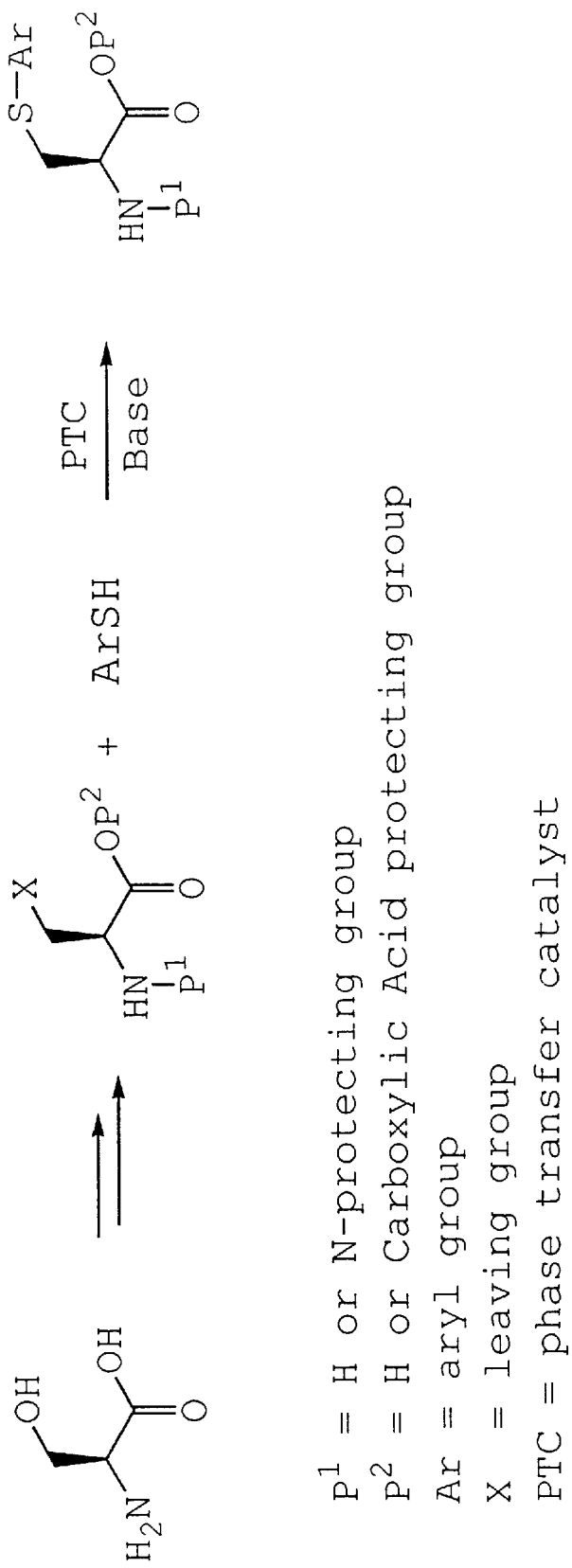
FIG. 3 illustrates yet another embodiment of the present invention for preparing a S-aryl cysteine compound which utilizes serine.

Yet another embodiment of the present invention provides a method for producing enantiomerically enriched S-aryl cysteine by contacting a serine derivative with an aryl thiol in the presence of a base, i.e., a substitution reaction, as shown in FIG. 3. As used in this invention, a "serine derivative" refers to a compound wherein the hydroxy group of serine is converted to a leaving group. Leaving groups according to the invention are groups that are attached to electrophiles and are displaced (e.g., through bond scission) in substitution reactions. Preferably, the leaving group is selected from the group consisting of a halide, tosylate and mesylate, more preferably the leaving group is selected from the group consisting of iodide, bromide, chloride, tosylate and mesylate, and most preferably the leaving group is selected from the group consisting of tosylate and mesylate. Although a leaving group may be "displaced", it can remain attached to the product of the substitution reaction by another covalent bond. For example, when the electrophile is an epoxide, only one of the bond between oxygen and carbon is broken in the substitution reaction. Oxygen, therefore, remains attached to the newly formed product of the substitution reaction. An electrophile is a moiety which loses a leaving group in a substitution reaction. In general an electrophile is a moiety which has an affinity for electrons. Electrophiles can be neutral or positively charged.

Useful bases for producing S-aryl cysteine from a reaction between a serine derivative with a leaving group and an aryl thiol include carbonates such as sodium carbonate, potassium carbonate and lithium carbonate; bicarbonates such as sodium bicarbonate, potassium bicarbonate and lithium bicarbonate; hydroxides such as sodium hydroxide, lithium hydroxide, calcium hydroxide, magnesium hydroxide and potassium hydroxide; sterically hindered amines such as triethyl amine and diisopropyl ethyl amine; hydrides such as sodium hydride, potassium hydride and lithium hydride; amides such as lithium diisopropyl amide and sodium diisopropyl amide; and other bases such as sodium hexamethyl disilazide. Preferably, the base is selected from the group consisting of carbonates, bicarbonates and hydroxides, more preferably the base is selected from the group consisting of carbonates and bicarbonates, and most preferably the base is a carbonate. It will be appreciated that the aryl thiol can be contacted with the base prior to adding any serine derivative with a leaving group, or the base can be added to a mixture of the aryl thiol and the serine derivative, or the aryl thiol can be added to the mixture of the base and the serine derivative.

The temperature of reaction can affect the enantiomeric excess of the product. To minimize loss of stereochemical integrity of the product and/or the starting material, the temperature of the substitution reaction between a serine derivative and the aryl thiol is maintained from about $-5°$ C. to about $35°$ C., preferably from about $15°$ C. to about $30°$ C. Preferably the reaction time is from about 1 h to about 48 h, more preferably from about 10 h to about 30 h, and most preferably from about 20 h to about 25 h.

The substitution reaction conditions of the present invention can include the presence of a phase transfer catalyst.

The term "phase transfer catalyst" means a catalyst or agent which is added to a reaction mixture of components, and operates to transfer one or more of the reacting components to a location where it can conveniently and rapidly react with another reacting component. Non-limiting examples of phase transfer catalysts or agents that may be employed are reviewed in C. M. Starks, C. L. Liotta, and M. Halpern, "Phase-Transfer Catalysis", Chapman & Hall, New York, 1994, which is incorporated herein in its entirety by reference. Exemplary phase transfer catalysts include tetrabutylammonium bromide (TBAB), tetrabutylammonium chloride (TBAC), Aliquat® 336, and tetrabutylphosphonium bromide (TBPB).

Any appropriate solvent can be used in the substitution reaction method of the present invention. However, when using a phase transfer catalyst, it is preferred that a relatively non-polar solvent be used. Exemplary relatively non-polar solvents which are useful in a substitution reaction method of the present invention include toluene, ethyl acetate and hexane. Preferably, the relatively non-polar solvent is selected from the group consisting of toluene, ethyl acetate and a mixture thereof.

The above method of the present invention can include protecting the amine group of the amino acid (e.g., cystine, cysteine, or serine). Any of the known amine protecting group can be used. Examples of some protecting groups are described in "Solid Phase Peptide Synthesis" by G. Barany and R. B. Merrifield in *Peptides*, Vol. 2, edited by E. Gross and J. Meienhoffer, Academic Press, New York, N.Y., pp. 100–118 (1980), and "Protective Groups in Organic Synthesis" by Green, T., John Wiley & Sons, Inc., New York, N.Y., 1981, pp. 218–287, which are incorporated herein in their entirety by reference. Exemplary N-amino protecting groups include methoxycarbonyl (i.e., a moiety of the formula —C(=O)OCH$_3$), acetyl, formyl, benzoyl, substituted benzoyls, FMOC, Bspoc, Bsmoc, t-butyloxycarbonyl (BOC), t-amyloxycarbonyl (Mcb), 2-(p-biphenylyl)propyl-2-oxycarbonyl (Bpoc), benzyloxycarbonyl (i.e., CBZ or a moiety of the formula —C(=O)OCH$_2$C$_6$H$_5$), phthaloyl, piperidino-oxycarbonyl, trifluoroacetyl and the like. Other N-amino protecting groups or blocking groups may include optionally protected α-amino acids which are linked with the carboxyl moiety of the α-amino acids. Preferably the amine protecting group is selected from the group consisting of methoxycarbonyl and benzyloxycarbonyl (i.e., CBZ). Amine protecting groups can be removed under various different conditions, including mild acidic or basic conditions. The preferred protecting groups are those which can be cleaved by an acid or a base, or reductive conditions. For example, the amine group can be protected as methyl carbamate or benzyl carbamate (i.e., CBZ), by contacting the amino acid with methyl chloroformate or benzyl chloroformate, respectively, in the presence of a base. Any base that can neutralize the acidic proton that is formed by the reaction of methyl chloroformate (or benzyl chloroformate) and the amino group can be used. Exemplary bases useful in protection of the amine group include carbonates such as sodium carbonate, potassium carbonate and lithium carbonate; bicarbonates such as sodium bicarbonate, potassium bicarbonate and lithium bicarbonate; hydroxides such as sodium hydroxide, lithium hydroxide, calcium hydroxide, magnesium hydroxide and potassium hydroxide; and sterically hindered amines such as triethyl amine and diisopropyl ethyl amine. Preferably, the base is selected from the group consisting of carbonates, bicarbonates and hydroxides, more preferably the base is selected from the group consisting of carbonates and bicarbonates, and most preferably the base is a bicarbonate. In one particular embodiment of the present invention, the amino group is protected by contacting the amino acid with benzyl chloroformate in the presence of sodium bicarbonate to provide N-benzyloxycarbonyl protected amino acid.

The above methods of the present invention can also include protecting the carboxylic acid group of the amino acid (e.g., cystine or cysteine). Any of the known carboxylic acid protecting group can be used. Protection of carboxylic acid moiety are described in "The Peptides," E. Gross and J. Meienhofer, Eds., Vol. 3, Academic Press, NY (1981), pp. 101–135, and "Protective Groups in Organic Synthesis" by Green, T., John Wiley & Sons, Inc., New York, N.Y., 1981, pp. 152–192, which are incorporated herein in their entirety by reference. Exemplary carboxylic acid protecting groups include esters such as alkyl esters including methyl, ethyl, tert-butyl, methoxymethyl, 2,2,2-trichloroethyl and 2-haloethyl; benzyl esters such as triphenylmethyl, diphenylmethyl, p-bromobenzyl, o-nitrobenzyl and the like; silyl esters such as trimethylsilyl, triethylsilyl, t-butyldimethylsilyl and the like; amides; and hydrazides. Other carboxylic acid protecting groups can include optionally protected α-amino acids which are linked with the amino moiety of the α-amino acids.

Alkyl groups according to the invention are aliphatic hydrocarbons which can be straight or branched chain groups having 1 to about 10 carbon atoms. Alkyl groups optionally can be substituted with one or more substituents, such as halo, aryl, hydroxy, alkoxy, carboxy, oxo and cycloalkyl. There may be optionally inserted along the alkyl group one or more oxygen, sulfur or substituted or unsubstituted nitrogen atoms. Exemplary alkyl groups include methyl, ethyl, i-propyl, n-butyl, t-butyl, n-pentyl, heptyl, benzyl, and octyl. Preferably the carboxylic acid protecting group is an ester, more preferably the carboxylic acid protecting group is an alkyl ester, and most preferably the carboxylic acid protecting group is selected from the group consisting of methyl ester and ethyl ester. In a particular embodiment of the present invention, the carboxylic acid of the amino acid is protected as a methyl ester by contacting the amino acid with thionyl chloride in the presence of methanol. Alternatively, the carboxylic acid is protected as methyl ester by contacting the amino acid with gaseous hydrochloric acid in the presence of methanol.

The above method can also include protecting both the amine group and the carboxylic acid group of the amino acid. It will be appreciated that the amine and carboxylic acid groups in the amino acid can be protected in any sequence.

A variety of S-aryl cysteines can be prepared by the process of the present invention. Preferably, the aryl group is substituted or unsubstituted aryl group selected from the group consisting of phenyl, naphthyl, pyridyl, furyl, thiophenyl, pyrazyl and pyrrolyl. More preferably, the aryl group is substituted or unsubstituted aryl group selected from the group consisting of phenyl, naphthyl and pyridyl, still more preferably the aryl group is selected from the group consisting of substituted and unsubstituted phenyl, and most preferably the aryl group is phenyl.

In another aspect of the present invention, the S-aryl cysteine which is recovered from the reaction mixture is further purified by distillation or crystallization process. In a particular embodiment of the present invention, S-aryl cysteine, which is recovered from the reaction mixture in a liquid form, is dissolved in toluene and crystallized from a relatively non-polar recrystallization solvent to afford a product of higher purity. Preferably, the non-polar recrystallization solvent is selected from the group consisting of hexanes, ethyl acetate, toluene, xylene, benzene, pentane, ethers and a mixture thereof. The S-aryl cysteine can be recovered as a salt. For example, adding an acid such as hydrochloric. acid; or an organic acid including tartaric acid, acetic acid, and/or citric acid, to S-aryl cysteine can result in the formation of a corresponding S-aryl cysteine salt which can be easily isolated. Alternatively, the free carboxylic acid moiety can react with a base to generate a carboxylate salt which can form a solid. In yet another alternative, the presence of both free amine and carboxylic moieties can result in the formation of a zwitterion which can precipitate as a solid.

Additional objects, advantages, and novel features of this invention will become apparent to those skilled in the art upon examination of the following examples thereof, which are not intended to be limiting.

EXAMPLES

Example 1

This example illustrates the preparation of N,N'-bis-benzyloxycarbonyl cystine dimethyl ester using thionyl chloride and cystine.

In a 500 mL jacketed round bottomed flask is placed cystine (20 g, 83.2 mmol) and methanol (250 mL). The reaction mixture is cooled to about 0° C. to about 5° C. and thionyl chloride (12.7 mL, 0.175 mol) is added while maintaining the temperature at less than about 10° C. At the end of the addition, the reaction is heated to reflux for about 4 hours and excess methanol is removed by distillation. As the product begins to precipitate, water was added followed by a slow addition of sodium bicarbonate (29.4 g, 0.35 mole) to the solution at less than about 5° C.

After the bicarbonate is added, benzyl chloroformate (25 mL, 0.175 mole) is slowly added. The reaction mixture is maintained at <5° C. for about 1 hour and slowly warmed to room temperature. The reaction mixture is heated to about 30° C. to about 40° C. and the organic phase is separated and the aqueous phase is washed with toluene (3×20 mL). The combined organic solution is washed once with sodium bicarbonate (25 mL), followed by 5% HCl, and saturated NaCl, dried over $MgSO_4$, and concentrated in vacuo by rotoevaporation to afford 44.25 g of an oil (0.0825 mole, 99.1% yield).

A portion of this oil (31.55 g) was recrystallized from EtOAc-hexanes to give a colorless solid (24.95 g, 79.1% yield).

mp 70–72° C. Assayed at 97.5% by A/N HPLC.

Example 2

This example illustrates the preparation of N,N'-bis-benzyloxycarbonyl cystine dimethyl ester using MeOH/HCl and cystine.

To a cold (from about –5° C. to about –10° C.) solution of methanol (100 mL) was bubbled HCl gas. About 11.0 g of HCl gas was absorbed into the solution. To a slurry of cystine in about 100 mL of methanol was added the above prepared HCl/Methanol solution. The mixture was heated to reflux. After about one hour, a clear solution was obtained. The mixture was heated to reflux for a total of about 4 hours, cooled to room temperature and transferred to a one neck round bottomed flask. Concentration of the mixture by rotoevaporation afforded white solids.

The white solids were suspended in about 400 mL of toluene. A solution of $NaHCO_3$ (31.5 g) in about 300 mL of water was added to give a clear two phase solution. Benzyl chloroformate (25.0 mL, 0.175 mole) was added dropwise at about 16° C. to about 18° C. The reaction mixture was then stirred at about 16° C. to about 18° C. for about 4 hours.

The aqueous phase was separated and extracted with toluene (3×50 mL). The combinedd toluene extracts were washed with water, dilute sodium carbonate solution, 5% HCl solution, and saturated sodium chloride solution. The organic phase was dried over $MgSO_4$ and concentrated in vacuo to give an oil. The oil was dissolved in ethyl acetate (100 mL). Hexanes (175 mL) was added and the mixture was seeded. The solution was stirred at room temperature overnight. The product was filtered, washed with a hexanes:EtOAc (9:1, 100 mL) mixture and dried under vacuum at about 45° C. to afford the product in 87.4% yield, 39.0 g, assayed at 98.5% A/N by HPLC.

Example 3

This example illustrates the preparation of N-CBZ S-phenyl-L-cysteine methyl ester using crude N,N'-bis-benzyloxycarbonyl cystine dimethyl ester.

Into a 250 mL round bottomed flask was added N,N'-bis-benzyloxycarbonyl cystine dimethyl ester (12.7 g, 237 mmol), copper powder (3.08 g) and dimethylformamide (130 mL). The stirred mixture was heated to about 70° C. Bromobenzene, i.e., phenyl bromide, (10 mL, 95 mmol) was charged to an addition funnel and added dropwise to the reaction mixture at about 70° C. to about 80° C. over 30 minutes. The reaction mixture was kept at about 75° C. to about 80° C. for 35 minutes, warmed to about 90° C. for 25 minutes, heated to about 100° C. for 4 hours, and then at about 110° C. for another 48 hours.

The reaction was monitored by thin layer chromatography. The reaction mixture was cooled to about 50° C. and DMF was distilled off under reduced pressure at about 50° C. to about 60° C. where 80 mL of distillate was recovered. The reaction mixture was diluted with toluene (150 mL) and water (50 mL) The resulting mixture was heated to reflux for 30 minutes and the solution was quickly filtered over a pad of celatom (a filter agent comprising diatomaceous earth or infusorial earth). The celatom pad was washed with excess toluene and the mixture was diluted with water. The phases were separated and the toluene phase was washed with water, 10% HCl/water (100 mL, v/v), and saturated sodium chloride.

The resulting solution was concentrated by rotoevaporation to afford a light yellow oil. The oil was dissolved in toluene (15 mL) and seeded to induce crystallization. Hexanes (15 mL) was added followed by another 60 mL of hexahes, and the slurry was stirred overnight at room temperature. The product was filtered, washed with excess hexanes, and air. dried to afford a colorless solid (66.7% yield, or 80.7% yield based on starting material assay of 82%; mp 62–64° C.).

Example 4

This example illustrates the preparation of N-CBZ S-phenyl-L-cysteine methyl ester using purified N,N'-bis-benzyloxycarbonyl cystine dimethyl ester.

Copper powder (4.62 g), bromobenzene (15.0 mL, 142 mmol), and DMF (55 mL) was charged to a 250 mL 3-neck round bottomed flask. The resulting mixture was heated to about 110° C. using an external oil bath. To the stirred mixture was added a solution of purified N,N'-bis-benzyloxycarbonyl cystine dimethyl ester (19.05 g, 35.5 mmol, 97.5% by assay) in DMF (40 mL) over 2 hours and 30 minutes. The resulting mixture was stirred at about 110° C. for about 18 hours and then at 130±2° C. for about 24 hours.

The resulting mixture was cooled to about 65° C. and DMF was distilled off under reduced pressure (50–60 mmHg) until a thick slurry was formed. The mixture was diluted with toluene (150 mL) and heated to about 70° C. to about 75° C. for 15–20 minutes. The solution was quickly filtered over a pad of celatom and the celatom pad was washed with warm (70° C.) toluene. The toluene phase was washed with water (2×100 mL), 10% aqueous HCl (1×100 mL), water (1×10 mL) and saturated sodium chloride (1×100 mL).

The reddish brown solution was dried over anhydrous magnesium sulfate. The solution was filtered through a pad of Filtrol-13® (a filter agent made of acid activated clays which is available from Filtrol Corp., Los Angeles, Calif.) to afford yellow solids. The filtrol pad was washed with toluene (100 mL). Toluene was distilled under reduced pressure at about 40° C. to about 45° C. until an oil was obtained. The oil was dissolved in toluene (25 mL), hexanes (25 mL) was added and the mixture was seeded to precipitate out the desired product. Hexanes (200 mL) was added and the resulting mixture was stirred at room temperature for 2.5 days. The product was filtered, washed with excess hexanes and dried under vacuum at about 45° C. to afford the desired product in 66.9% yield (16.4 g, 98.3% by A/N assay).

Concentration of the mother liquors afforded 6.2 grams of an oil (41% product by A/N assay).

Example 5

This example illustrates the preparation of N-CBZ S-phenyl-L-cysteine methyl ester from N-CBZ-cysteine methyl ester.

Into a round bottomed flask was charged N-CBZ-cysteine methyl ester (5.4 g, 20.0 mmol), copper oxide (2.8 g), and bromobenzene (4.2 mL, 39.9 mmol) in dimethylformamide (25.0 mL). The reaction mixture was heated to reflux (145±2° C.) for 19 hours. Analysis by HPLC revealed 25.9% N-CBZ S-phenyl-L-cysteine methyl ester and 6.0% N-CBZ S-benzyl cysteine methyl ester.

Example 6

This example illustrates the preparation of N-CBZ S-phenyl-L-cysteine from N,N'-bis-benzyloxycarbonyl cystine.

A mixture of N,N'-bis-benzyloxycarbonyl cystine (3.81 g, 7.5 mmol), copper powder (0.95 g, 15.0 mmol), and bromobenzene (3.32 mL, 4.95g, 31.5 mmol) in dimethylformamide (20 mL) was heated to about 120° C. for about 19 hours. The resulting mixture was cooled to about 80° C. and dimethylformamide was removed by vacuum distillation at about 80° C. to about 95° C., where 15 mL of distillate was collected.

The resulting residue was diluted with toluene (70 mL) and stirred for about 1 hour at about 70° C. to about 75° C. The product was filtered and washed with excess toluene. The combined organic phases were washed with 10% aqueous HCl (1×70 mL), water (2×70 mL), saturated sodium chloride (1×70 mL), and the solution was dried over anhydrous magnesium sulfate.

The solution was filtered, the resulting filter cake was washed with excess toluene, and the organic solution was concentrated to afford 4.8 g of a light brown oil which solidified upon standing. 96.6% yield, 4.8 g, assayed at 96.33% by A.N. HPLC, containing 3.67% A.N. of the corresponding S-benzyl acid.

$^1$H NMR (300 MHz, CDCl$_3$/TMS) δ 3.43 (ddd, 2H), 4.63 (br s, 1H), 5.08 (s, 2H), 5.02 (br d, 1H), 7.45–7.2 (m, 10H).

After the filter cake was washed with toluene, the filter cake was further washed with 2×40 mL of toluene at about 60° C. The filter cake may be reused for another coupling reaction.

Phase Transfer Catalyzed Nucleophilic Displacement Reactions:

Phase-transfer catalyzed nucleophilic displacement of N-protected serine ester mesylate (Ms) or tosylate (Tos) using aryl thiols to prepare the corresponding N-protected S-aryl-L-cysteine derivatives is provided in the following representative experimental descriptions. Tables 1–4 provide results from various alkylation reactions employing different reactions conditions, including variations in the type of phase-transfer catalyst, reaction stoichiometry, base, and substrates.

TABLE 1

Phase Transfer Alkylation with Thiophenol (at 25° C.)

|  | 1 | 2 | 3 | 4 |
|---|---|---|---|---|
| Substrate | Mesylate | Mesylate | Mesylate | Mesylate |
| PhSH (equiv.) | 1.0 | 1.0 | 1.0 | 1.0 |
| PTC | TBAB | TBAB | TBAB | TBAB |
| PTC (mol %) | 5.0 | 10 | 10 | 10 |
| Base | K$_2$CO$_3$ | NaHCO$_3$ | 18% NaOH | K$_2$CO$_3$ |
| Base (equiv.) | 1.20 | 1.10 | 1.10 | 2.00 |
| Solvent (10 mL) | Toluene | Toluene | Toluene | Toluene |
| Time (h) | 22 | 23 | 23.5 | 22 |
| Crude Yield (g) | — | — | 0.800 | — |
| Chrom Yield (g) | 0.255 | 0.411 | 0.713 | 0.301 |
| Chrom Yield (%) | 24.5 | 39.4 | 68.4 | 28.9 |
| R:S | 99.5:0.5 | 98.4:1.6 | 80.3:19.7 | 99.1:0.9 |
| ee (%) | 99.0 | 96.8 | 60.6 | 98.2 |

TABLE 2

Phase Transfer Alkylation with Thiophenol (at 25° C.)

|  | 5 | 6 | 7 | 8 |
|---|---|---|---|---|
| Substrate | Mesylate | Mesylate | Mesylate | Mesylate |
| PhSH (equiv.) | 1.1* | 1.0 | 1.0 | 1.0 |
| PTC | TBAB | TBAB | TBAB | TBPB |
| PTC (mol %) | 10 | 10 | 5.0 | 5.0 |
| Base | 18% NaOH | K$_2$CO$_3$ | K$_2$CO$_3$ | K$_2$CO$_3$ |
| Base (equiv.) | 1.04 | 2.00 | 1.50 | 1.50 |
| Solvent (10 mL) | Toluene | EtOAc | EtOAc | EtOAc |
| Time (h) | 22.5 | 19 | 23 | 19 |
| Crude Yield (g) | 0.940 | 0.959 | 0.954 | 0.967 |
| Chrom Yield (g) | 0.848 | 0.787 | 0.830 | 0.878 |
| Chrom Yield (%) | 81.4 | 75.5 | 79.6 | 84.3 |
| R:S | 90.3:9.7 | 90.2:9.8 | 89.4:10.6 | 89.8:10.2 |
| ee (%) | 80.6 | 80.4 | 78.8 | 79.6 |

*Preformed NaSPh

TABLE 3

Phase Transfer Alkylation with Thiophenol (at 25° C.)

|  | 9 | 10 | 11 | 12 |
|---|---|---|---|---|
| Substrate | Tosylate | Tosylate | Tosylate | Tosylate |
| PhSH (equiv.) | 1.0 | 1.0 | 1.0 | 1.5 |
| PTC | — | TBAB | TBPB | TBAB |
| PTC (mol %) | — | 5.0 | 5.0 | 5.0 |
| Base | K$_2$CO$_3$ | K$_2$CO$_3$ | K$_2$CO$_3$ | K$_2$CO$_3$ |
| Base (equiv.) | 1.50 | 1.50 | 1.50 | 1.50 |
| Solvent (10 mL) | Toluene | Toluene | Toluene | Toluene |
| Time (h) | 22.5 | 17 | 24 | 22 |
| Crude Yield (g) | 1.159 | 0.959 | 0.986 | 1.042 |
| Chrom Yield (g) | 0.171 | 0.877 | 0.858 | 0.918 |
| Chrom Yield (%) | 16.4 | 84.2 | 82.3 | 88.0 |
| R:S | 98.4:1.6 | 99.2:0.8 | 99.8:0.2 | 97.3:2.7 |
| ee (%) | 96.7 | 98.4 | 99.6 | 94.6 |

TABLE 4

Phase Transfer Alkylation with Thiophenol (at 25° C.)

|  | 13 | 14 | 15 | 16 |
|---|---|---|---|---|
| Substrate | Mesylate | Mesylate | Mesylate | Mesylate |
| PhSH (equiv.) | 1.0 | 1.0 | 1.0 | 1.5 |
| PTC | TBPB | TBAB | Aliquat ® 336 | Aliquat ® 336 |
| PTC (mol%) | 5.0 | 5.0 | 4.0 | 4.0 |
| Base | K$_2$CO$_3$ | K$_2$CO$_3$ | K$_2$CO$_3$ | K$_2$CO$_3$ |
| Base (equiv.) | 1.50 | 1.50 | 1.50 | 1.50 |
| Solvent (mL) | Toluene (10) | Tol:EtOAc (8:2) | Toluene (10) | Toluene (10) |
| Time (h) | 20.5 | 18.5 | 41 | 3.0 |
| Crude Yield (g) | 0.948 | 0.959 | 0.992 | 0.974 |

TABLE 4-continued

Phase Transfer Alkylation with Thiophenol (at 25° C.)

|  | 13 | 14 | 15 | 16 |
|---|---|---|---|---|
| Chrom Yield (g) | 0.409 | 0.841 | 0.795 | 0.817 |
| Chrom Yield (%) | 39.2 | 80.7 | 76.3 | 78.4 |
| R:S | 98.2:1.8 | 93.9:6.1 | 90.9:9.1 | 92.9:7.1 |
| ee (%) | 96.4 | 87.8 | 81.8 | 85.8 |

Example 7

This example illustrates the preparation of N-CBZ S-phenyl-L-cysteine methyl ester by the displacement of N-benzyloxycarbonyl-O-p-toluenesulfonyl-L-serine methyl ester.

A mixture of 1.23 g (3.02 mmol) of N-benzyloxycarbonyl-O-p-toluenesulfonyl-L-serine methyl ester, anhydrous potassium carbonate powder (0.626 g, 4.53 mmol, 1.5 equiv.), tetrabutylphosphonium bromide (TBPB, 51 mg, 0.151 mmol, 5 mole %), thiophenol (0.31 mL, 3.02 mmol), and toluene was stirred at about 25° C. for about 24 hours.

Water (20 mL) was added and the phases were separated. The organic phase was washed with water (20 mL), dried over magnesium sulfate, and filtered. Concentration on a rotoevaporator at about 30° C. to about 35° C. and 30 mmHg afforded an oil. Drying of the oil under vacuum at about 25° C. for about 18 hours (at ca. 0.5 mmHg) afforded a colorless solid (0.986 g, 94.6% yield).

$^1$H NMR (300 MHz, CDCl$_3$/TMS) δ 3.4 (m, 2H), 3.02 (s, 3H), 4.63 (m, 1H), 5.08 (s, 2H), 5.62 (br d, 1H), 7.2–7.42 (m, 10H). $^{13}$C NMR (75 MHz, CDCl$_3$) δ 170.67, 155.58, 137, 136.18, 131.05, 129.02, 128.5, 128.16, 128.06, 127.08, 67.03, 53.71, 52.39, 36.98.

Example 8

This example illustrates the preparation of N-CBZ S-phenyl-L-cysteine methyl ester by the displacement of N-benzyloxycarbonyl-O-methanesulfonyl-L-serine methyl ester:

Thiophenol (0.31 mL, 0.333 g, 3.02 mmol) was added via syringe to a suspension of N-benzyloxycarbonyl-O-methanesulfonyl-L-serine methyl ester (1.00 g, 3.02 mmol), powdered anhydrous K$_2$CO$_3$, tetrabutylammonium bromide (TBAB, 49 mg, 0.151 mmol, 5 mole %), and toluene (20 mL). The suspension was stirred at about 25° C. for about 22 hours. Water (20 mL) was added and the phases were separated. The organic phase was washed with 20 mL water, 10 mL of ethyl acetate was added, dried over magnesium sulfate, and filtered. Concentration on a rotoevaporator in vacuo at about 35° C. and about 35 mmHg afforded a wet colorless solid.

The solid was dissolved in methylene chloride and separated on a 4 mm silica gel chromatotron plate. The product was separated using hexanes (250 mL), 10% ethyl acetate in hexanes (800 mL), ethyl acetate (200 mL), and methanol (200 mL). The combined fractions were concentrated on a rotoevaporator at about 75 mmHg and at about 30° C. to about 35° C. The residual oil was triturated with hexanes and the solids were dried under vacuum (<0.5 mmHg) for about 7.5 hours at about 25° C. to afford 0.255 g of a colorless solid (24.5% chromatographed yield, 98.2%R:0.50%S by assay).

$^{13}$C NMR Spectrum for the Mesylate: (75 MHz, CDCl$_3$) δ 168.85, 155.80, 136.00, 128.52, 128.24, 128.08, 68.66, 67.26, 53.51, 53.03, 37.20.

Example 9

This example illustrates the preparation of N-CBZ S-phenyl-L-cysteine methyl ester from N-benzyloxycarbonyl-O-p-toluenesulfonyl-L-serine methyl ester.

A mixture of 12.31 g (30.2 mmol) of N-benzyloxycarbonyl-O-p-toluenesulfonyl-L-serine methyl ester (commercially available from Synthetec, 6.26 g, 45.3 mmol, 1.5 equivalents) of anhydrous powdered potassium carbonate (Aldrich Chemical Co., Milwaukee, Wis., catalog No. 34,782-5), 512 mg (1.51 mmol, 5.0 mol %) tetrabutylphosphonium bromide, 100 mL toluene, and 3.1 mL (3.33 g, 30.2 mmol) thiophenol was stirred at about 25° C. for about 31 h.

Reaction progress was followed by LC. After 1 h, 85% tosylate remaining, 5 h (55%), 25 h (4.6%), 30 h (tosylate not detected). Water (40 mL) was added and the layers separated. The organic layer was washed with 20 mL water then distilled at atmospheric pressure to reduce the volume of toluene (bath about 125° C.) (under dry N$_2$). The weight of solution remaining after the distillation was 28.75 g.

The solution after cooling contained a small amount of solid residue (salts from residual water in the toluene after the phase split). These solids were removed by gravity filtration. The mother liquor was slowly diluted with 80 mL of hexanes. The precipitate was suction filtered, washed with 20 mL hexanes, and dried under vacuum at about 25° C. for about 22 h to afford 8.309 g of colorless solid, mp. 64.7–65.2° C.

Theoretical Yield: 10.431 g. Percent Yield: 79.7%. LC Assay for Optical Purity: 0.1% S.

Example 10

This example illustrates the preparation of N-CBZ S-phenyl-L-cysteine methyl ester from N-benzyloxycarbonyl-O-p-toluenesulfonyl-L-serine methyl ester.

A mixture of 30.00 g (73.63 mmol) of N-benzyloxycarbonyl-O-p-toluenesulfonyl-L-serine methyl ester (commercially available from Synthetec, 15.27 g, 110 mmol, 1.5 equivalents) of anhydrous powdered potassium carbonate, 1.249 g (3.68 mmol, 5.0 mol %) tetrabutylphosphonium bromide, 150 mL toluene, and 7.6 mL (8.11 g, 73.6 mmol) thiophenol was stirred at about 25° C. for about 8 days.

Water (75 mL) was added and the layers separated. The organic layer was washed with 75 mL water then distilled at reduced pressure to reduce the volume of toluene (heating bath at about 125° C., under dry N$_2$). The weight of solution remaining after the distillation was 41.6 g.

The residual oil was diluted with 100 mL of hexanes. The precipitate was suction filtered, washed on the funnel with 75 mL hexanes, then dried under vacuum at about 25° C. for about 19 hours to afford 22.75 g of colorless solid.

Theoretical Yield: 25.43 g; Percent Yield: 89.5%; LC Assay for Optical Purity: 0.5% S; LC Assay for Chemical Purity: 97.9% Thiocarbaester.

Example 11

This example illustrates the preparation of N-CBZ S-(3-methoxyphenyl)-L-cysteine methyl ester from N,N'-bis-benzyloxycarbonyl cystine dimethyl ester and 3-bromoanisole.

Starting material, N,N'-bis-benzyloxycarbonyl cystine dimethyl ester 3.0 g (5.6 mmol) was dissolved in anhydrous DMF at a solvent ratio of 10:1. To the solution is added 2.0 equivalents of copper powder (0.71 g, 11.2 mmol) and 4.0 equivalents of 3-bromoanisole (4.1 g, 22.3 mmol), and the mixture is heated to about 120° C. to about 130° C. After stirring overnight the reaction mixture was checked by HPLC and was determined to have <5% starting material. The reaction mixture was cooled and the DMF as well as most of the excess 3-bromoanisole was removed under reduced pressure. The crude mixture was dissolved with 10 volumes of toluene and the copper and copper salts were removed by filtration.

The filtrate was washed once with 30 mL of a 50:50 mixture (10% $NH_4OH$, 15% w/w $NH_4Cl$) followed by one wash with saturated brine. The organic layer is concentrated under reduced pressure and the crude product was purified by silica gel chromatography resulting in 2.73 g of a light yellow oil (65% yield).

$^1$H NMR (300 MHz, $CDCl_3$) δ 3.38 (m, 1H), 3.57 (s, 2H), 3.75 (s, 3H), 3.80 (s, 3H), 5.15 (m, 2H), 5.6 (d, 1H), 6.7–7.4 (m, 9H).

Example 12

This example illustrates the preparation of N-CBZ S-(2-(6-methoxynaphthalenyl))-L-cysteine methyl ester from N,N'-bis-benzyloxycarbonyl cystine dimethyl ester and 2-bromo-6-methoxynaphthalene.

Starting material, N,N'-bis-benzyloxycarbonyl cystine dimethyl ester, 2.75 g (5.12 mmol) was dissolved in anhydrous DMF at a solvent ratio of 10:1. To the solution is added 2.0 equiv. of copper powder (0.65 g, 10.2 mmol) and 4.37 equiv. of 2-bromo-6-methoxynaphthalene (5.3 g, 22.4 mmol), and the mixture is heated to about 120° C. to about 130° C. After stirring overnight the reaction mixture was checked for completion by HPLC and was determined to have <5% starting material. The reaction mixture was cooled and the DMF was removed under reduced pressure. The crude mixture was dissolved with about 10 volumes of toluene and the copper and copper salts were removed by filtration.

The filtrate was washed once with 30 mL of a 50:50 mixture (10% $NH_4OH$, 15% w/w $NH_4Cl$) followed by one wash with saturated brine. The organic layer was concentrated under reduced pressure and the crude product was purified by silica gel chromatography resulting in a light brown oil 1.96 g (45% yield).

$^1$H NMR (300 MHz, $CDCl_3$) δ 3.4 (m, 5H), 3.85 (s, 3H), 4.65 (m, 2H), 5.02 (m, 1H), 5.65 (d, 1H), 7.78–7.03 (m, 11H).

Example 13

This example illustrates the preparation of N-CBZ S-(3-pyridyl)-L-cysteine methyl ester from N,N'-bis-benzyloxycarbonyl cystine dimethyl ester and 3-bromopyridine.

Starting material, N N,N'-bis-benzyloxycarbonyl cystine dimethyl ester, 3.0 g (5.6 mmol) was dissolved in anhydrous DMF at a solvent ratio of 10:1. To the solution was added 2.0 equiv. of copper powder (0.71 g, 11.2 mmol) and 4.0 equiv. of 3-bromopyridine (3.5 g, 22.3 mmol), and the mixture is heated to about 120–130° C. After stirring overnight the reaction mixture was checked with HPLC and was determined to have <5% starting material. The reaction mixture was cooled and the DMF was removed under reduced pressure. The crude mixture was dissolved with 10 volumes of toluene and the copper and copper salts were removed by filtration.

The filtrate was washed once with 30 mL of a 50:50 mixture (10% $NH_4OH$, 15% w/w $NH_4Cl$) followed by one wash with saturated brine. The organic layer was concentrated under reduced pressure and the crude product was purified by silica gel chromatography resulting in 2.05 g of a reddish-brown oil (53% yield).

$^1$H NMR (300 MHz, $CDCl_3$) δ 3.15 (m, 2H), 3.75 (s, 3H), 4.63 (m, 1H), 5.15 (s, 2H), 5.66 (d, 1H), 7.25–7.75 (m, 9H).

Example 14

This example illustrates the preparation of N,N'-bis-(3-acetoxy-2-methylbenzoyl)cystine dimethyl ester from cystine dimethyl ester hydrochloride and 3-acetoxy-2-methylbenzoyl chloride.

Cystine dimethyl ester hydrochloride (5.36 g, 0.0157 mole), 3-acetoxy-2-methylbenzoyl chloride (6.67 g, 0.0314 mole), and triethyl amine (6.35 g, 0.0628 mole) were dissolved in dichloromethane (50 mL) and the resulting mixture was stirred at ambient temperature overnight. The organic phase was washed with 2 N hydrochloric acid (2×20 mL) and then with water (2×20 mL).

The organic layer was dried over $MgSO_4$ and concentrated on a rotary evaporator to give a light yellow solid. Trituration of the solid with 100 mL of toluene gave a light yellow crystalline solid, which was isolated by filtration and dried at about 50° C. under vacuum to give N,N'-bis-(3-acetoxy-2-methylbenzoyl)cystine dimethyl ester (4.30 g, 44.1% yield). A second crop was obtained by silica gel column chromatography of the mother liquors, eluting with 50% methylene chloride in ethyl acetate.

$^1$H NMR (300 MHz, $CDCl_3$) δ 2.23 (s, 3H), 2.32 (s, 3H), 3.30 (app dq, 2H, J=6.0, 9.0 Hz), 3.77 (s, 3H), 5.02 (m, 1H), 6.71 (d, 1H, J=6.0 Hz), 7.08 (app dd, 1H, J=3.0, 9.0 Hz), 7.21 (t, 1H, J=9H), 7.31 (app dd, 1H, J=3.0, 9.0 Hz).

Example 15

This example illustrates the preparation of N-(3-acetoxy-2-methylbenzoyl)-S-phenyl-L-cysteine methyl ester from N,N'-bis-(3-acetoxy-2-methylbenzoyl)cystine dimethyl ester and bromobenzene.

Into a 3-necked 50 mL round bottomed flask equipped with an overhead stirrer under nitrogen atmosphere was added N,N'-bis-(3-acetoxy-2-methylbenzoyl)cystine dimethyl ester (4.3 g, 0.00693 g), bromobenzene (6.5 g, 4.4 mL, 0.0416 mole), copper (0.92 g, 0.0145 mole), and dimethyl formamide (25 mL) The resulting mixture was heated to 120±3° C. for about 19 hours.

Volatiles were removed by distillation at about 80–85° C. on a rotary evaporator under reduced pressure to afford a brown residue. The residue was dissolved in 30 mL of dichloromethane and washed with 3 N hydrochloric acid (20 mL), followed by washing with water (2×20 mL). The organic phase was dried over $MgSO_4$, filtered, and concentrated on a rotary evaporator to afford a light yellow solid (3.6 g, 53% yield).

$^1$H NMR (300 MHz, $CDCl_3$) δ 2.17 (s, 3H), 2.25 (s, 3H), 3.43 (dq, 2H, J=3.0, 15.0 Hz), 3.50 (s, 3H), 4.93 (dt, 1H, J=6.0, 9.0 Hz), 6.65 (d, 1H, J=6.0 Hz), 7.0–7.4 (m, 8H).

Example 16

This example illustrates a method for synthesizing N-CBZ S-phenyl-L-cysteine methyl ester from N,N'-bis-benzyloxycarbonyl cystine dimethyl ester using copper powder and catalytic $CuBr_2$.

N,N'-Bis-benzyloxycarbonyl cystine dimethyl ester (4.00 g, 7.45 mmol), copper powder (4.72 gm, 74 mmol, from Acupowder International, LLC, Union, N.J.), cupric bromide ($CuBr_2$, 1.84 gm, 8.23 mmol), phenyl bromide (2.4 mL, 22.7 mmol), and dimethylformamide (24 mL) were combined in a 50 mL round bottomed flask. The resulting stirred mixture was immersed in a preheated oil bath at about 140° C. for about 3 hours.

HPLC analysis showed 1.5% carbacystine remaining. Dimethylformamide was removed by distillation at about 120° C. and at about 50 mmHg of pressure. The residue was diluted with 15 mL of toluene and filtered through a pad of celatom to remove the solids. The filtrate was washed twice with 30 mL of 1 M HCl and once with 30 mL of water. Toluene was removed on a rotary evaporator under reduced pressure.

The residue was crystallized by dissolving in approximately 5 mL toluene and adding hexane (50 mL) slowly at about 40° C. to initiate precipitation. The mixture was cooled to ambient temperature, filtered and the product was washed with 20 mL of hexanes. The solid was dried under vacuum at about 50° C. to give 3.05 gm of an off-white solid (59% yield). m.p. 61.9–63.5° C.

$^1$H NMR (300 MHz, $CDCl_3$) δ 3.37 (dd, 2H, 3 Hz, 3 Hz), 3.48 (s, 3H), 4.59 (dt, 1H, 3Hz, 9 Hz), 5.03 (s, 2H), 5.59 (d, 1H, 6 Hz), 7.1–7.4 (m, 10H).

Example 17

This example illustrates a method for preparing N-CBZ S-phenyl-L-cysteine methyl ester from N,N'-bis-benzyloxycarbonyl cystine dimethyl ester using copper powder and catalytic $Br_2$.

To a 25 mL 2 neck round bottomed flask purged with nitrogen and equipped with condenser was added N,N'-bis-benzyloxycarbonyl cystine dimethyl ester (2.00 gm, 3.73 mmol), copper powder (0.5 gm, 7.87 mmol), dimethylformamide (10 mL), and phenyl bromide (2.0 mL, 1.34 gm, 8.54 mmol).

The resulting stirred mixture was heated to about 115° C. to about 125° C. for about 22 hours. Two drops of bromine were added to the reaction and the resulting mixture was heated for another about 22 hours where no starting material remained. HPLC analysis revealed 88.4% (A.N.) of the desired product, N-CBZ S-phenyl-L-cysteine methyl ester.

Example 18

This example illustrates the preparation of N-CBZ S-phenyl-L-cysteine methyl ester starting with N,N'-bis-benzyloxycarbonyl cystine dimethyl ester in dimethyl sulfoxide at 130° C.

Into a 250 mL round bottomed flask equipped with a thermometer, mechanical stirrer and nitrogen inlet was added N,N'-bis-benzyloxycarbonyl cystine dimethyl ester (13.25 g, 0.025 mol), copper powder (4.0 g, 0.0625 mole) and copper (II) bromide (0.34 g, 0.00152 mole). To the mixture was added bromobenzene (31.6 mL, 0.3 mole) and dimethyl sulfoxide (67 mL, dried over 4 A sieve).

The mixture was stirred and heated to about 130° C. for about 1 hour and 15 minutes. No starting material was detected. Analysis by HPLC showed 94.3% N-CBZ S-Phenyl-L-cysteine methyl ester and no starting material. The resulting mixture was cooled to about 120° C. and stirred for additional about 18 hours. HPLC analysis showed 81.7% N-CBZ S-Phenyl-L-cysteine methyl ester, 3.9% benzyl alcohol, 4.2% diphenyl sulfide, and 3.4% N-CBZ S-phenyl-L-cysteine benzyl ester.

Example 19

This example illustrates the preparation of N-CBZ S-phenyl-L-cysteine methyl ester starting with N,N'-bis-benzyloxycarbonyl cystine dimethyl ester in dimethyl sulfoxide at about 100° C.

Into a 250 mL round bottomed flask equipped with a thermometer, mechanical stirrer and nitrogen inlet was added N,N'-bis-benzyloxycarbonyl cystine dimethyl ester (6.7 g, 0.013 mol), copper powder (2.0 g, 0.0315 mole) and copper (II) bromide (0.2 g, 0.895 mmole). To the mixture was added bromobenzene (15.8 mL, 23.56 g, 0.15 mole) and dimethyl sulfoxide (33 mL, dried over 4 A sieve).

The mixture was stirred and heated to about 100° C. for about 18 hours. Analysis by HPLC showed 88.8% N-CBZ S-Phenyl-L-cysteine methyl ester and no starting material. The resulting mixture was cooled to room temperature.

HPLC analysis showed 88.8% N-CBZ S-Phenyl-L-cysteine methyl ester, 2.5% benzyl alcohol, 0.5% methyl carbamate, 2.1% diphenyl sulfide, and 1.2% diphenyl disulfide.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for enantioselectively preparing S-aryl-L-cysteine of the formula:

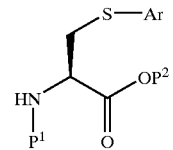

comprising contacting a compound of the formula:

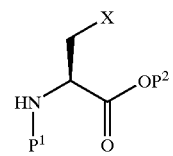

with an aryl thiol in the presence of a base in a non-polar reaction solvent to produce said S-aryl-L-cysteine;
wherein
Ar is a substituted or unsubstituted aryl group selected from the group consisting of phenyl, naphthyl, pyridyl, furyl, thiophenyl, pyrazyl, and pyrrolyl;
$P^1$ is an amine protecting group;
$P^2$ is a carboxylic acid protecting group; and
X is a halide, mesylate or tosylate;
and wherein said method produces said S-aryl cysteine in enantiomeric excess of greater than about 96%.

2. The method of claim 1, wherein said method further comprises a presence of a phase transfer catalyst.

3. The method of claim 2, wherein said phase transfer catalyst is selected from the group consisting of tricaprylylmethylammonium chloride, TBAB, and TBPB.

4. The method of claim 1, wherein $P^1$ is selected from the group consisting of moieties of the formula —C(=O)$OCH_3$ and —C(=O)$OCH_2C_6H_5$.

5. The method of claim 1, wherein $P^1$ is methyl.

6. The method of claim 1, wherein said base is selected from the group consisting of sodium hydroxide, sodium bicarbonate, and potassium carbonate.

7. The method of claim 1, further comprising a reaction solvent, wherein said reaction solvent is selected from the group consisting of toluene, ethyl acetate and mixtures thereof.

8. The method of claim 1, wherein X is selected from the group consisting of mesylate and tosylate.

9. A method of claim 1, wherein said S-aryl-L-cysteine is used in a synthesis of an HIV protease inhibitor.

10. A method for enantioselectively preparing S-aryl-L-cysteine of the formula:

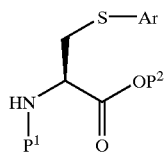

comprising contacting a compound of the formula:

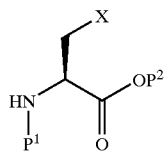

with an aryl thiol in the presence of a base and a phase transfer catalyst to produce said S-aryl-L-cysteine in enantiomeric excess of greater than about 96%;

wherein

Ar is a substituted or unsubstituted aryl group selected from the group consisting of phenyl, naphthyl, pyridyl, furyl, thiophenyl, pyrazyl, and pyrrolyl;

$P^1$ is selected from the group consisting of moieties of the formula —C(=O)OCH$_3$ and —C(=O)OCH$_2$C$_6$H$_5$;

$P^2$ is methyl; and

X is mesylate or tosylate.

11. The method of claim 10, wherein said phase transfer catalyst is-selected from the group consisting of tricaprylylmethylammonium chloride, TBAB, and TBPB.

12. The method of claim 10, wherein said base is selected from the group consisting of sodium hydroxide, sodium bicarbonate, and potassium carbonate.

13. A compound selected from the group consisting of N,N'-bis-(3-acetoxy-2-methylbenzoyl)-L-cystine dimethyl ester, N-(3-acetoxy-2-methylbenzoyl)-S-phenyl-L-cysteine methyl ester, and N,N'-bis-methoxycarbonyl-(L)-cystine dimethyl ester.

* * * * *